United States Patent
Sorensen et al.

[11] Patent Number: 5,618,296
[45] Date of Patent: Apr. 8, 1997

[54] TISSUE MORCELLATOR SYSTEM AND METHOD

[75] Inventors: John T. Sorensen, Costa Mesa; Frans Limonta, Laguna Hills; Larry A. Dial, Chino Hills, all of Calif.

[73] Assignee: Endomedix Corporation/Box 330, Huntington Beach, Calif.

[21] Appl. No.: 507,054

[22] Filed: Jul. 24, 1995

[51] Int. Cl.$^6$ .................................................. A61B 17/39
[52] U.S. Cl. ........................................ 606/180; 606/167
[58] Field of Search ..................... 606/167, 114, 606/180, 184; 604/22; 128/749, 751, 752, 753, 754

[56] References Cited

U.S. PATENT DOCUMENTS

| | | | |
|---|---|---|---|
| 3,938,505 | 2/1976 | Jamshidi | 128/753 |
| 4,324,262 | 4/1982 | Hall | 128/756 |
| 4,368,734 | 1/1983 | Banko | 606/170 |
| 4,461,305 | 7/1984 | Cibley | 606/180 |
| 4,867,576 | 9/1989 | Boyd | 383/33 |
| 5,074,867 | 12/1991 | Wilk | 606/128 |
| 5,076,276 | 12/1991 | Sakurai et al. | 128/660 |
| 5,190,561 | 3/1993 | Graber | 606/127 |
| 5,197,968 | 3/1993 | Clement | 606/115 |
| 5,207,697 | 5/1993 | Carusillo et al. | 606/167 |
| 5,215,521 | 6/1993 | Cochran et al. | 604/22 |
| 5,224,930 | 7/1993 | Spaeth et al. | 604/33 |
| 5,234,439 | 8/1993 | Wilk et al. | 606/114 |
| 5,256,132 | 10/1993 | Snyders | 600/16 |
| 5,275,609 | 1/1994 | Pingleton et al. | 606/170 |
| 5,290,303 | 3/1994 | Pingleton et al. | 606/170 |
| 5,301,684 | 4/1994 | Ogirala | 128/754 |
| 5,423,330 | 6/1995 | Lee | 128/753 |

FOREIGN PATENT DOCUMENTS

| | | |
|---|---|---|
| 1272412 | 1/1962 | France. |
| WO9211816 | 7/1992 | WIPO. |

*Primary Examiner*—Michael Powell Buiz
*Assistant Examiner*—Patrick W. Rasche
*Attorney, Agent, or Firm*—Stetina Brunda & Buyan

[57] ABSTRACT

A morcellation system and method for reducing and removing tissue or other matter contained within a mammalian body. A portal apparatus, having a central opening, is inserted into a small incision. Thereafter, a hollow-bore morcellator device is nestable within the central opening of the portal device. The hollow-bore morcellator device includes a rotatable shaft which extends downwardly into the body cavity, and upon which an annular cutting ring is mounted. An elongate suction probe is passable downwardly through the hollow-bore morcellator device, and is usable to engage (by suction force) a mass of tissue or other matter, and to repeatedly lift such mass into contact with the rotating annular cutting ring of the morcellator shaft. A tissue containment chamber may be positioned on the proximal end of the suction probe such that segments of tissue or matter separated by the annular cutting ring may be aspirated through the suction probe and collected within the collection chamber. The morcellator system may be utilized in conjunction with a flexible tissue containment bag. The tissue containment bag is preferably engageable with the portal apparatus to facilitate insertion of the morcellator device thereinto. Also, the system may include a pressurization system for passing positive pressure gas into the tissue containment bag. The passing of gas into the bag may be coordinated with the removal of gas withdrawn through the suction probe to ensure that the containment bag remains fully expanded during the suction operation.

36 Claims, 10 Drawing Sheets

TISSUE MORCELLATOR SYSTEM AND METHOD

FIELD OF THE INVENTION

The present invention pertains generally to medical equipment and more particularly to a system for morcellating matter within a body cavity, and for removing such morcellated matter from the body cavity through a minimal access incision.

BACKGROUND OF THE INVENTION

The development of modern endoscopic technology has enabled physicians to endoscopically view and excise or resect various organs, tumors and other matter contained within body cavities. Such endoscopic surgical procedures are typically performed by inserting an endoscope and the necessary operative instruments through minimal access incisions of approximately 1 cm in length. However, the organ, tumor or other matter which is excised or resected during such procedures is often too large to be removed from the body through the previously-formed minimal access incision(s). Thus, in order to remove such excised or resected matter from the body it is often necessary to either enlarge the size of the incision(s) or to reduce the size of the excised/resected matter, in order to facilitate its removal through the originally-formed minimal access incision(s). Included among the above-described endoscopic surgical procedures are various laparoscopic surgeries wherein a laparoscope and various instruments are inserted into the abdominal cavity through small abdominal incisions and are utilized to locate and excise or resect a diseased organ (e.g., gallbladder, uterus, bowel section, appendix, etc.), tumor and/or other matter (e.g., gallstones, uterine myomas, ovarian cysts, etc.) which is desired to be removed from the abdominal cavity.

In general, laparoscopic surgical procedures are conducted by initially inserting an inflation needle into the peritoneum and passing pressurized carbon dioxide through the inflation needle to create a distended pneumoperitoneum. Thereafter, a primary minimal access incision, such as a 1 cm incision or puncture, is formed in the periumbilical region of the abdominal wall. A primary laparoscopic portal or trocar is then inserted through such periumbilical puncture or incision. A laparoscope is then inserted into the pneumoperitoneum through the primary umbilical portal or trocar. One or more secondary trocars (i.e., "accessory portals") may also be inserted through additional incisions or punctures formed at secondary sites in the abdominal wall, to facilitate insertion into the abdomen and use of various operative instruments (e.g., blunt forceps, cutting instruments, cannulas, etc.). The operative instruments are then manipulated and utilized by the surgeon to perform the desired intra-abdominal surgical procedure while he/she views the procedure by way of the laparoscope. In some procedures, the laparoscope may be moved, during the course of the procedure, from the primary umbilical portal to an accessory trocar or portal, thereby freeing the primary portal for passage of additional instrumentation, and for subsequent use as a passageway for removal of the surgically excised tissue or matter. In recognition of the problem associated with removing tissue or matter from a body cavity through an incision or puncture which is smaller than the tissue or matter to be removed, the prior art has included a number of instruments designed to reduce the size of the tissue or matter within the body cavity in order to facilitate its extraction and removal through a relatively small minimal access incision or puncture. Examples of such prior art devices for intracorporeal reduction of tissue or other matter include those described in the following patents and patent publications: U.S. Pat. No. 4,324,262 (Hall), entitled Aspirating Culture Catheter And Method of Use; U.S. Pat. No. 4,368,734 (Banko), entitled Surgical Instrument; U.S. Pat. No. 5,074,867 (Wilk), entitled Surgical Instrument Assembly And Related Surgical Method; U.S. Pat. No. 5,076,276 (Sakurai et al.), entitled Ultrasound Type Treatment Apparatus; U. S. Pat. No. 5,190,561 (Graber), entitled Tissue And Organ Extractor; U.S. Pat. No. 5,215,521 (Cochran et al.), entitled Laparoscopy Organ Retrieval Apparatus And Procedure; U.S. Pat. No. 5,224,930 (Spaeth et al.), entitled Trocar System For Facilitating Passage Of Instruments Into A Body Cavity Through A Minimal Access Incision; U.S. Pat. No. 5,234,439 (Wilk et al.), entitled Method And Instrument Assembly For Removing Organ; U.S. Pat. No. 5,256,132 (Snyders), entitled Cardiac Assist Envelope For Endoscopic Application; U.S. Pat. No. 5,275,609 (Pingleton et al.), Surgical Cutting Instrument; U.S. Pat. No. 5,290,303 (Pingleton et al.), entitled Surgical Cutting Instrument; International Patent Nos. WO 92/11816 (Sorensen et al.), entitled Method And Device For Intracorporeal Liquidization Of Tissue And/Or Intracorporeal Fragmentation Of Calculi During Endoscopic Surgical Procedures; French Patent No., 1,272,412 (Kreie) entitled Cathéter Urétral Avec Corbeille Expansible Pour L'Extraction De Calculs Rénaux.

In particular, the prior art has included the laparoscopic morcellator described in U.S. Pat. No. 5,215,521 (Cochran et al.), entitled LAPAROSCOPY ORGAN RETRIEVAL APPARATUS AND PROCEDURE. The device described in U.S. Pat. No. 5,215,521 is purportedly useable to reduce tissue or other matter contained within an intracorporeally positioned entrapment envelope. The entrapment envelope comprises a flexible sac which is deployable into the body cavity. The entrapment envelope may incorporate wire guides or pneumatic means to facilitate opening of the envelope after it has been introduced into the body cavity. The organ, tissue or other matter to be removed is placed into the envelope, using manipulative instruments. The neck of the envelope is then exteriorized through the laparoscopic incision and the tissue morcellator device is inserted through the exteriorized neck of the envelope. The morcellator device described in U.S. Pat. No. 5,215,521 comprises an elongate tubular sheath which has a suction port on its proximal end and an open distal end. A drive shaft extends longitudinally through the morcellator sheath and is provided with a rotary cutting head on its distal end. The rotary cutting head is positioned within the open distal end of the tubular sheath. A drive means or hand crank is connected to the proximal end of the drive shaft to rotatably drive the drive shaft and cutting head within the surrounding tubular sheath. A suction side arm extends perpendicularly from a proximal portion of the tubular sheath. When suction is applied to the suction side arm, the reduced tissue fragments are aspirated through the space which exists between the inner wall of the tubular sheath and the rotating drive shaft which extends through the tubular sheath. Such tissue fragments are drawn out of the suction side arm, and into an attendant tissue containment canister. The application of vacuum through the tubular sheath ostensibly serves not only to aspirate the fragment tissue into the containment canister, but also to assist in bringing the organ or tissue into cutting contact with the rotating head, without requiring dangerous plunging motions of the morcellator device.

Despite the prior efforts to design tissue morcellation systems, there remains a need in the art for an improved high speed morcellation system that may be utilized to rapidly reduce and remove tissues which are tough in consistency (e.g., uterine myomas) as well as other tissues, tumors, organs or matter from anatomical passageways and/or body cavities. Also, there remains a need in the art for a tissue morcellator device which is capable of reducing and removing various tissues in pieces which are sufficiently large in size to permit adequate gross pathological evaluation.

SUMMARY OF THE INVENTION

The present invention provides a tissue morcellator system and method. The tissue morcellator system is made up of a number of component devices, each of which constitutes a separate invention in itself and has separate utility apart from the overall system.

The basic components of the tissue morcellation system of the present invention comprise: a) a portal apparatus insertable into a mammalian body through a small incision and having a central opening formed therein; b) a hollow-bore morcellator device which is insertable through the opening of the portal apparatus, and c) a suction probe which is passable through the hollow-bore of the morcellator device, and which remains moveable back and forth therein. The suction probe is initially advanceable to engage, by suction pressure, a mass of tissue or other matter. The suction probe is then retractable so as to lift said mass of tissue or matter into contact with a cutting surface of the morcellator device so as to sever the mass of tissue or other matter. The severed portion or bolus of the tissue or other matter is then aspirated through the suction probe and is thus removed from the body. Such back and forth movement (i.e., advancement and retraction) of the suction probe may be repeated until the entire mass of tissue or other matter has been removed from the body.

Further in accordance with the invention, the system may incorporate a pliable containment sac or bag which is deployable into a body cavity, and useable to hold and contain the tissue or other matter which is to be reduced and removed by the morcellator system. The preferred tissue containment sac incorporates an opening member, such as an inflatable air bladder, about the mouth of the sac to effect opening of the sac after it has been deployed into the body cavity. A tubular introducer may be provided for use as a conduit for insertion of the containment sac or bag into the body.

Further in accordance with the invention, the portal apparatus of the morcellator system may be configured and constructed to receive and hold open the mouth of the containment sac such that, when the morcellator device is inserted through the opening of the portal apparatus, the morcellator device will be thereby concurrently inserted into the interior of the sac.

Further in accordance with the invention, the system may include a pressurization conduit, passageway or system for infusing pressurized fluid (e.g., air) into the interior of the containment sac or bag after it has been deployed in the body cavity, to maintain the pressure within the sac or bag at a level which is greater than the surrounding pressure in the body cavity, thereby preventing the sac or bag from collapsing during use. Such fluid infusion passageway, conduit or system may be at least partially formed within the portal apparatus of the morcellator system, or may comprise a separate tube or conduit which is insertable, apart from the portal apparatus into the interior of the containment sac or bag. If used in conjunction with the above-described morcellator system, the pressurization conduit, passageway or system may be coordinated with the source of negative pressure or vacuum connected to the suction probe, or otherwise regulated and controlled, to insure that the mass flow of pressurized fluid infused into the interior of the sac or bag is at least equal to the mass flow withdrawn through the suction probe. This will cause the pressure within the sac or bag to remain above the pressure of the pneumoperitoneum surrounding the exterior of the sac, thereby maintaining the sac in non-collapsed configuration. Further objects and advantages of the invention will become apparent to those skilled in the art upon reading and understanding of the following detailed description and the accompanying drawings.

DETAILED DESCRIPTION OF THE PREFERRED EMBODIMENTS

Figure 1:
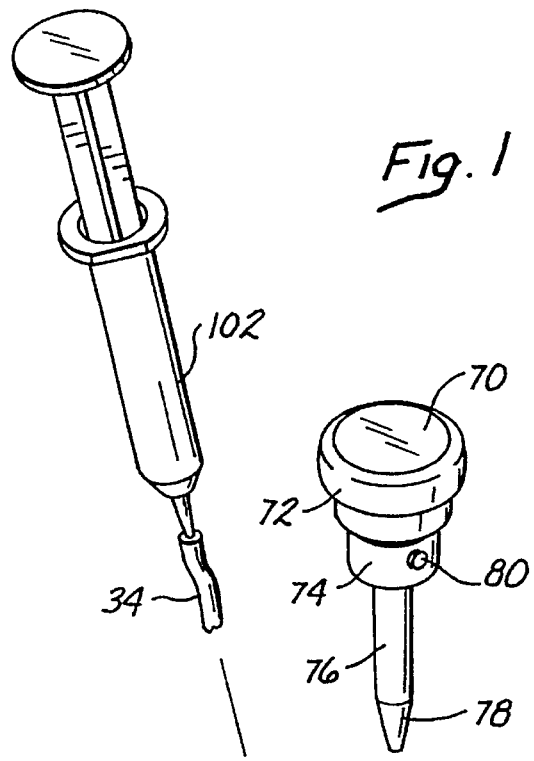
FIG. 1 is an exploded perspective view of one embodiment of a morcellator system of the present invention.
Figure 1:
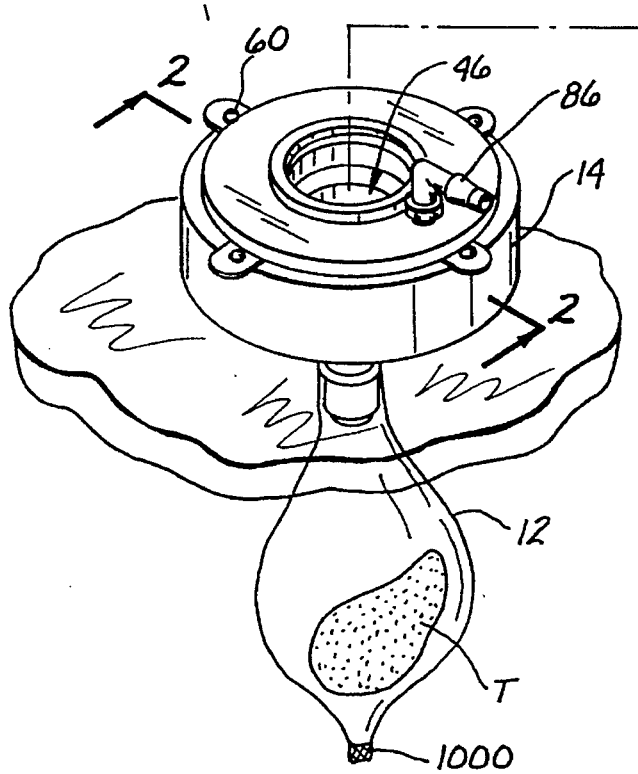
Figure 1:
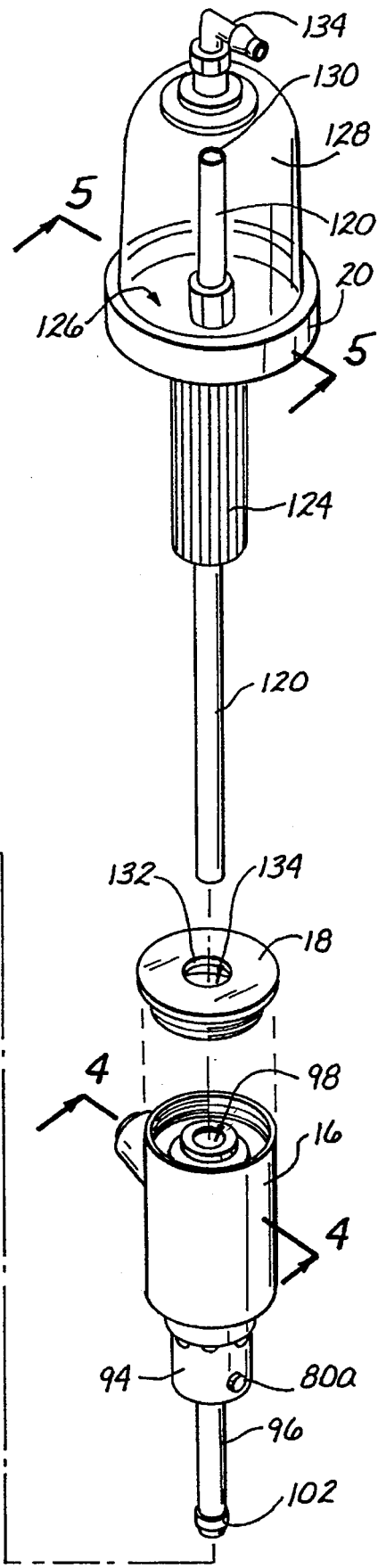

The following detailed description and the accompanying drawings are provided for purposes of describing and illustrating presently preferred embodiments of the invention only, and are not intended to limit the scope of the invention in any way.

With reference to the drawings, the preferred morcellator system 10 of the present invention comprises the following components:

a flexible tissue containment bag 12;

a morcellator-receiving/bag-pressurizing portal apparatus 14 which comprises an inner ring 62 positioned within an outer ring 52;

a hollow-bore morcellator device 16;

a pressure-maintaining seal element 18; and a suction probe/tissue containment chamber apparatus 20.

The individual components of the system 10, and the manner in which they operate, are more fully described herebelow:

i. Tissue/Matter Containment Sac

Figure 3:
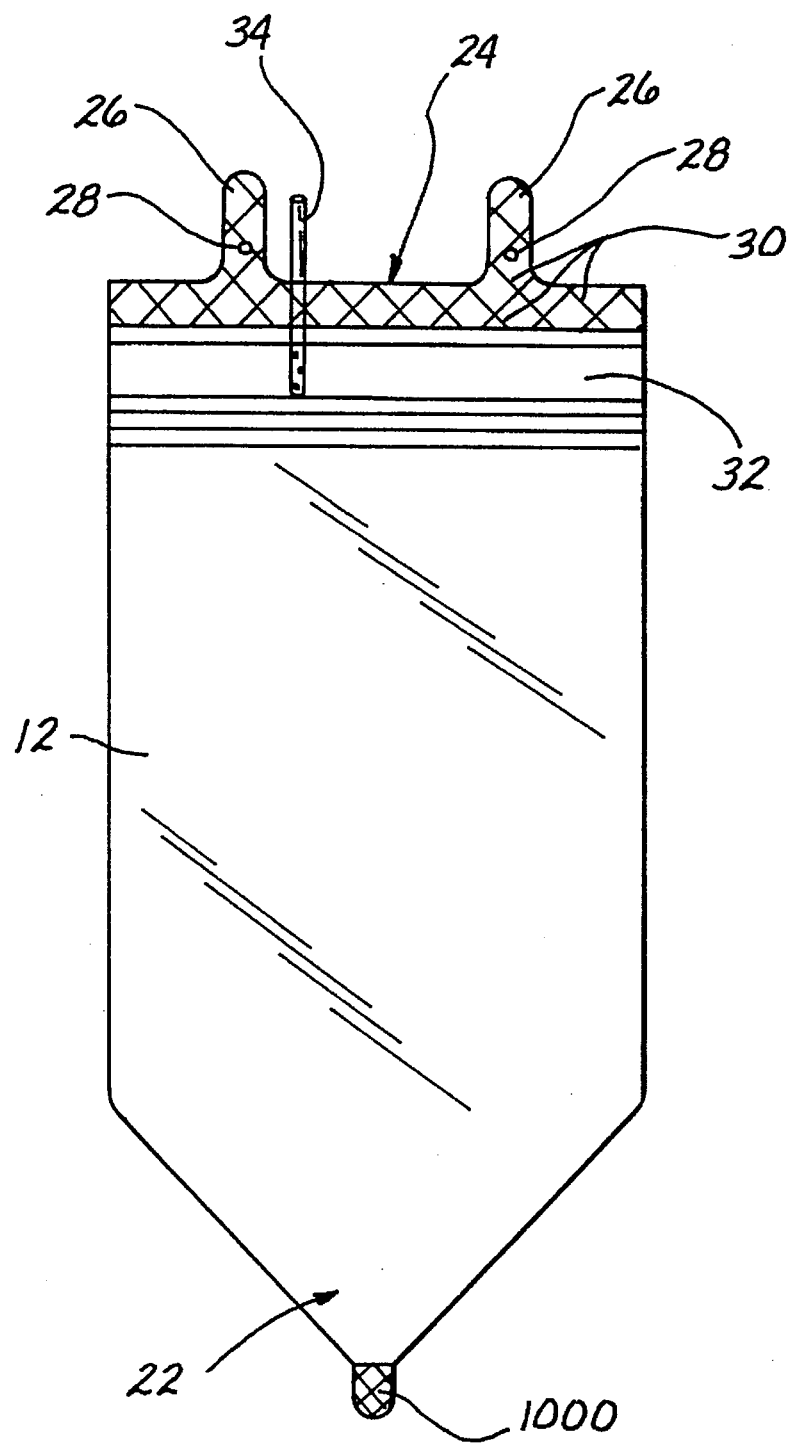
FIG. 3 is an elevational view of the tissue containment sac of the system shown in FIG. 1.

The preferred tissue/matter containment sac or bag 12, as shown in FIG. 3, comprises a clear or transparent pliable bag formed of polyurethane or other suitable plastic material. The bag 12 comprises a pouch having a tapered or "V" shaped bottom portion 22 and a top opening or mouth 24. A pliable tab 1000 extends downward from bottom portion 22 of the bag to facilitate grasping and pulling of the bag into a body cavity. A multiplicity of pliable tabs 26 extend upwardly from the top edge of the bag 12. Such tabs 26 have apertures 28 formed therein. Apertures 28 are configured and positioned to be fitted over corresponding engagement projections or bulbous lugs 60 formed on the morcellator-receiving, bag-pressurizing portal apparatus 14 so as to hold the mouth 24 of the bag 12 in an open configuration, in alignment with the opening of the portal apparatus 14. The specific manner in which the bag 12 fits onto, and is pressurized through, the portal apparatus 14 will be more fully described herebelow. Tabs 1000, 26 also provide locations where bag 12 can be safely grasped with surgical graspers for the purpose of manipulating bag 12 within the abdominal cavity without the potential for causing accidental punctures of bag 12, which would compromise its fluid-tight integrity.

A reinforcement material 30 such as wire mesh, nylon mesh, or other suitable reinforcing material may be incorporated into the upper portion of the bag 12, and/or tab 1000 and/or tabs 26 to prevent the upper portion of the bag 12 and/or tabs 26 and/or tab 1000, from tearing or ripping during use.

Also, the preferred bag 12 incorporates an opening apparatus or biasing member formed or located about the mouth 24 of the bag 12 to urge the mouth 24 of the bag 12 to an open configuration so as to facilitate emplacement of tissue or other matter into the bag. In the preferred embodiment, such opening apparatus or biasing member comprises an annular air bladder 32 formed about the upper portion of the bag 12, and having an air passage tube 34 connected thereto.

As shown in FIGS. 7a–7d the containment bag 12 may be inserted by way of a tubular introducer 100 which comprises a smooth plastic tube having a seal member 101, such as an elastomeric cap having a self-sealing slit or aperture formed therein, mounted on the proximal end of the tube. The bag 12 is initially packed in the lumen of the introducer 100 such that the pull tab 1000 protrudes slightly out of the distal end of the introducer 100. A grasper instrument 510 or other apparatus may then be used to pull the bag out of the introducer 100 and into the body cavity. The air passage tube 34 slides accordingly through the self sealing slit or aperture of the seal member 101 on the proximal end of the introducer.

Air or other gas may be injected through air passage tube 34 into the annular air bladder 32. Such inflation of the annular air bladder 32 will cause the mouth 24 of the bag 12 to open. Subsequent deflation of the annular air bladder 32 will allow the mouth 24 of the bag 12 to collapse or return to a closed configuration.

ii. Morcellator-Receiving/Bag-Pressurizing Portal Apparatus

Figure 2:
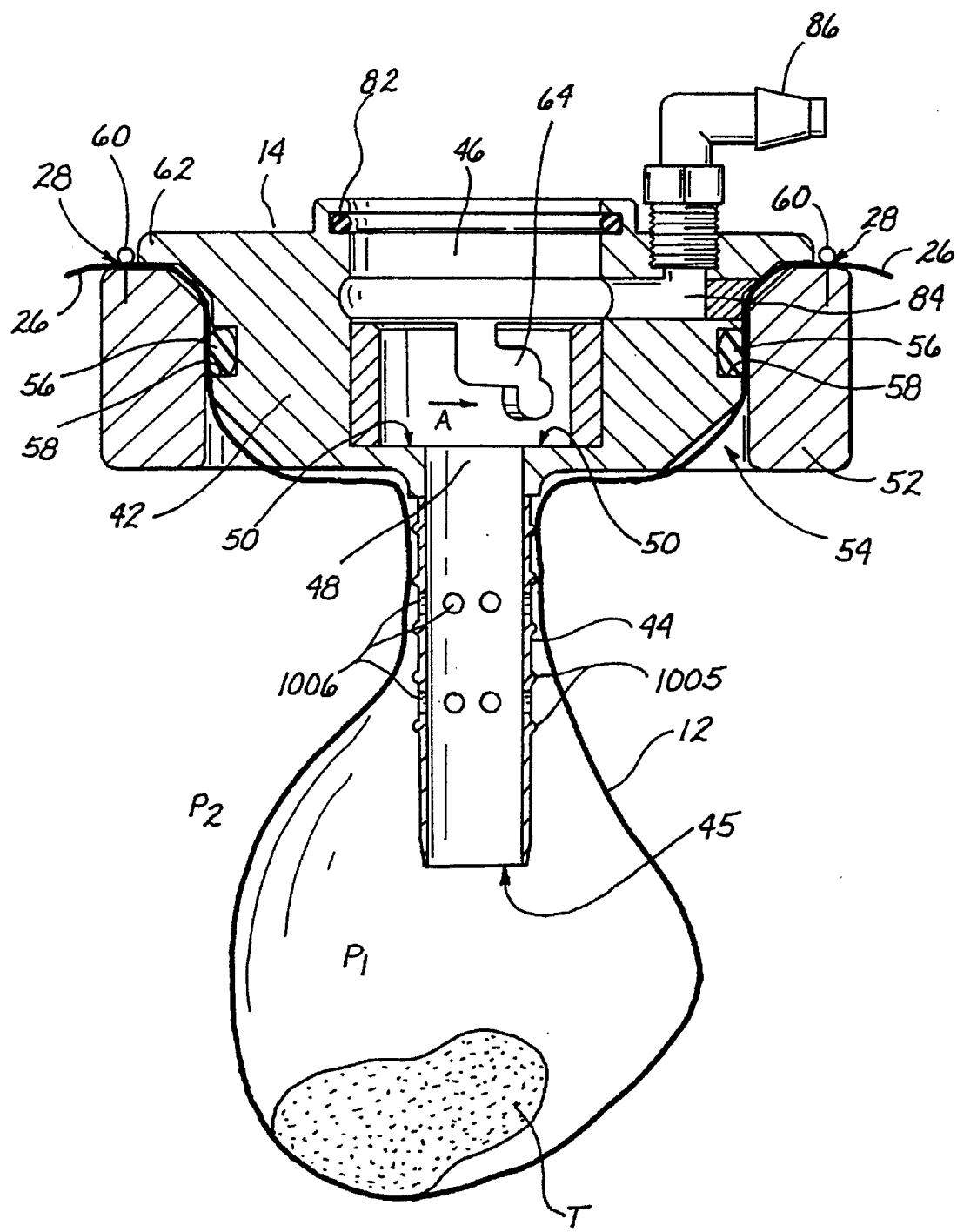
FIG. 2 is an enlarged sectional view of the portal apparatus of the system shown in FIG. 1, said portal apparatus being inserted into the mouth of a tissue containment bag to a) receive and support a morcellator device and b) facilitate pressurization of the interior of the tissue containment bag.
Figure 6:
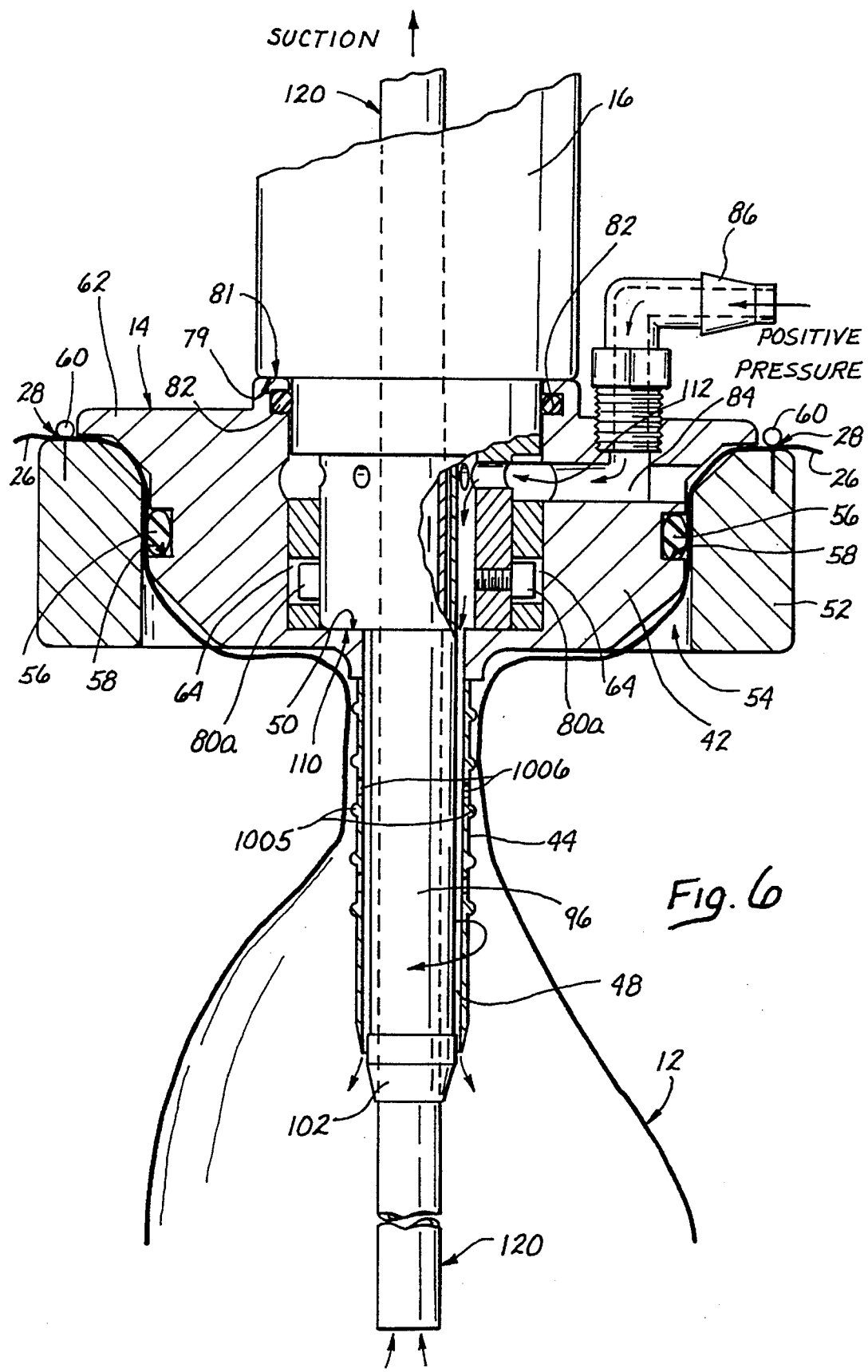
FIG. 6 is a partial cut-away longitudinal sectional view of the morcellator system of FIG. 1 wherein the portal apparatus is operatively inserted into the mouth of a tissue containment bag, the hollow-bore morcellator device is operatively inserted through the portal apparatus, and the suction probe/tissue containment chamber apparatus is operatively inserted through the hollow bore of the morcellator device.

The preferred portal apparatus 14 is shown in detail in FIGS. 1, 2 and 6. This preferred portal apparatus 14 is configured and constructed to support and hold the mouth of the containment bag 12 in an accessible, open configuration and to receive and support the morcellator device 16 such that the cutting aspect of the morcellator device 16 is operatively inserted and positioned within the bag 12. Also, the preferred portal apparatus 14 incorporates pressurization passageways through which pressurized gas may be passed into the interior of the containment bag 12, in accordance with this invention.

As shown, the preferred portal apparatus 14 is formed of inner and outer ring members 42, 52 which define a central passageway which extends downwardly through the portal apparatus 14 to facilitate insertion of the morcellator device 16 therethrough. The central passageway of the portal apparatus 14 is preferably configured to permit the morcellator device 16 to be nested therewithin and supported thereby. Accordingly, in the preferred embodiment shown, the portal apparatus 14 comprises the combination of a) a rigid inner ring member 42 and b) an outer ring member 52. The central passageway of the portal apparatus 14 is defined in part by an upper central opening 46, having a first diameter $D_1$, which extends downwardly into the top of the inner ring member 42. A lower central opening 48, having a smaller diameter $D_2$, extends downwardly from the bottom of the upper central opening 46, through the tubular projection 44, and opens through the distal end thereof. The area of transition from the diameter $D_1$ of the upper central opening 46 to the smaller diameter $D_2$ of the lower central opening 48 forms an annular abutment shoulder or ridge 50, as shown. This annular shoulder or ridge 50 facilitates seating of the morcellator device 16 within the central passageway of the portal apparatus 14.

The inner ring member 42 of the portal apparatus 14 seats within the larger central bore 54 of the outer ring member 52, preferably entrapping or compressing the open mouth 24 of the containment sac 12 therebetween. An O-ring 56 is positioned within a notch 58 formed about the outer surface of the inner ring member 42. When the inner ring member 42 of the portal apparatus 14 is seated or nested within the outer ring member 52, the O-ring 56 will make sealing contact with the inner surface of the outer ring member 52 or the intervening material of the sac 12 positioned therebetween, thereby forming a seal to prevent leakage of gas from the interior of the bag 12 through the space between the inner ring member 42 and the bag 12.

A plurality of connector members, such as bulbous lugs 60 are formed at spaced-apart positions around the top edge of the outer ring member 52. Such bulbous lugs 60 are sized, configured and positioned to receive and connect to corresponding connector members such as apertures 28 formed about the mouth 24 of the containment bag 12. In the embodiment shown, the mouth 24 of the tissue containment bag 12 is drawn upwardly through the central bore 54 of the ring member 52. The holes 28 formed in the tabs 26 of the bag 12 may be passed over the bulbous lugs 60 such that the lugs 60 will hold the mouth 24 of the bag 12 in an open configuration within the central bore 54 of the outer ring member 52.

Thereafter, the inner ring member 42 of the portal apparatus 14 may be inserted downwardly into the mouth 24 of the bag 12 such that the annular lip or rim 62 of the inner ring member 42 engages and seats within the outer ring member 52. When so positioned, the hollow tubular projection 44 which protruded downwardly from the inner ring member 42 will extend downwardly into the interior of the tissue containment bag 12, as shown in FIG. 2. The upper portion of the bag 12 is thus compressively held between the outer ring member 52 and inner ring member 42. The hollow tubular projection 44 which extends into the interior of the bag 12 has formed on its outer surface a series of frictional retention protrusions in the form of annular ridges 1005 or a continuous helical external screw thread. The frictional retention protrusions are frictionally engaged by the taught surrounding incision to help prevent the tubular projection 44 from inadvertently slipping or retracting in the proximal direction.

A plurality of holes 1006 are formed in the wall of tubular projection 44 to communicate pressurized gas flow from lower central opening 48 into the interior of the bag 12.

An obturator 70, shown in FIG. 1, is insertable into the upper 46 and lower 48 central openings of the portal apparatus 40 to close off the portal apparatus 40 prior to insertion of the morcellator device 16. Such obturator 70 preferably comprises a rigid disc-shaped upper plug portion 72 having a first lower portion 74 of a first diameter $D_1$ and a second lower portion 76 of a second diameter $D_2$. Such obturator 70 is thus insertable into the inner ring member 42 of the portal apparatus 14 such that the shoulder formed by the transition from diameter $D_1$ of first lower portion 74 to diameter $D_2$ of second lower portion 76 of the obturator 70 rests on annular abutment shoulder 50, and the second lower portion 76 of obturator 70 extends downwardly through the lower central opening 48 of the portal apparatus 14. A blunt tapered tip 78 formed on the distal end of the second lower portion 76 may extend out of and beyond the distal end opening 45 of the tubular projection 44 of the portal apparatus 14. The protrusion of such blunt tapered distal tip 78 of the obturator 70 serves to facilitate concurrent insertion of the portal apparatus 14/obturator 70 combination into the containment bag 12.

An engagement lug 80 is formed on the outer surface of the first lower portion 74 of the obturator 70. Such engagement lug 80 is sized, configured and positioned to fit into, and frictionally engage, the serpentine engagement keyway 64. By such arrangement, the obturator 70 may be initially inserted downwardly, and subsequently rotated in the direction of arrow A, so as to cause the engagement lug 80 to travel fully into, and to frictionally engage within, engagement keyway 64, thereby holding the obturator 70 in position within the upper and lower central openings 46, 48 of the portal apparatus 14. An O-ring 82 is positioned within a notch or groove formed about the inner surface of the upper central opening 46, such that said O-ring 82 will abut against the outer surface of the obturator 70, when inserted into the portal apparatus 14. The abutment of the O-ring 82 against the outer surface of the obturator 70 prevents leakage of gas around the obturator 70 when so inserted.

A pressurized gas inlet passageway 84 is formed in the inner ring member 42 of the portal apparatus 14 to permit pressurized gas to be infused or passed into the interior of the bag 12. A tubing connector 86 is provided to facilitate connection of a pressure inlet tube to gas inlet passageway 84.

iii. Hollow-Bore Morcellator Device

The preferred hollow-bore morcellator device 16 is a motorized tissue cutting device which is configured and constructed to seat or nest within the central passageway of the portal apparatus 14, after the obturator 70 has been removed therefrom. The preferred construction of the hollow-bore morcellator device 16 is shown in detail in FIG. 4.

As shown, the morcellator device 16 comprises a rigid, generally cylindrical motor housing 90 having a hollow-shaft, brushless, DC electric motor 92 mounted therewithin. A hollow, rotatable motor shaft 96 extends downwardly from the motor housing, as shown. An annular cutting ring 102 is threadably or otherwise attached on the distal end 100 of the motor shaft 96. A hollow bore 98 extends fully through the morcellator motor 92, longitudinally through the rotatable motor shaft 96, and through the cutting ring 102.

The inner diameter of the annular cutting ring 102 is preferably of slightly reduced size relative to the inner diameter of the hollow bore 98 which extends through the drive shaft 96 and motor 92 of the morcellator device 16. The annular cutting ring 102 has a sharpened distal cutting edge 104 which, when rotating at sufficient velocity will sever a cylindrical plug or bolus of tissue each time a mass of tissue is brought into contact therewith. The cutting edge 104 may be provided with a simple continuous sharp bevel, or may alternately be provided with a sharp scalloped, or toothed surface. The specific configuration and type of cutting edge 104 employed will be optimally selected for efficacy in cutting the particular type of tissue or matter being removed.

A rigid engagement lug 80*a* is formed on the outer surface of the lower housing portion 94 of the morcellator device 16. Such rigid engagement lug 80*a* is sized, configured and constructed to fit into, and frictionally engage, a serpentine engagement groove or keyway 64 formed in the portal apparatus 14. Turning of the morcellator device 16 in the direction of arrow A will facilitate seating of the engagement lug 80*a* into locking engagement in the lower-most portion of engagement keyway 64. By such arrangement, the hollow-bore morcellator device 16 is firmly seated and held in its intended operative position within the central passageway of the portal apparatus 14. When so positioned, the lower surface 110 of the lower housing portion 94 of the morcellator device 16 abuts against the annular shoulder or ridge 50 of the portal apparatus 14, O-ring 82 seals against the outer surface 1001 of the lower housing portion 94 of morcellator device 16, and the rotating drive shaft 96 extends downwardly through the lower tubular projection 44 of portal apparatus 14, such that the annular cutting ring 102 of the morcellator device 16 is located slightly beyond the open distal end 45 of the lower tubular projection 44 of portal apparatus 14.

A plurality of holes 112 are formed in lower housing portion 94 of the morcellator device 16 to communicate pressurized gas flow from the outer surface of lower housing portion 94 through the annular space 1004 between inner surface 1003 of lower housing portion 94 and the outer surface of rotatable motor shaft 96. By such arrangement, when hollow-bore morcellator device 16 is operably located within portal apparatus 14 (as shown in FIG. 6), air or other gas pressure may be pumped through the gas inlet passageway 84, radially inward through holes 112, downwardly through annulus 1004, downwardly through a small annular space which exists between the outer surface of rotatable motor shaft 96 and the adjacent inner surface of the tubular projection 44 of the portal apparatus 14, and radially outward through holes 1006 in tubular projection 44 of the portal apparatus 14. This enables the positive pressure gas to pass into the interior of the bag 12 to cause the pressure $P_1$ within the bag 12 to be greater than the pressure $P_2$ in the surrounding body cavity (e.g., pneumoperitoneum). Such difference between pressure $P_1$ within the bag and the pressure $P_2$ surrounding the bag is maintained at a sufficient level to prevent the bag 12 from collapsing inwardly during use.

When the hollow bore motor 92 is energized, the hollow shaft 96 will be caused to rotate, causing concurrent rotation of annular cutting head 102.

One significant advantage of the morcellator device 16 described hereabove is that the hollow-bore 98 extends fully through the motor 92, and permits cylindrical plugs or boluses of tissue to be withdrawn upwardly through a straight passageway and into an attendant collection chamber. In this regard, the cylindrical plugs or boluses of tissue may be maintained intact, and will be sufficiently large to permit competent pathological examination thereof.

iv. Pressure-Maintaining Seal Element

Figure 4:
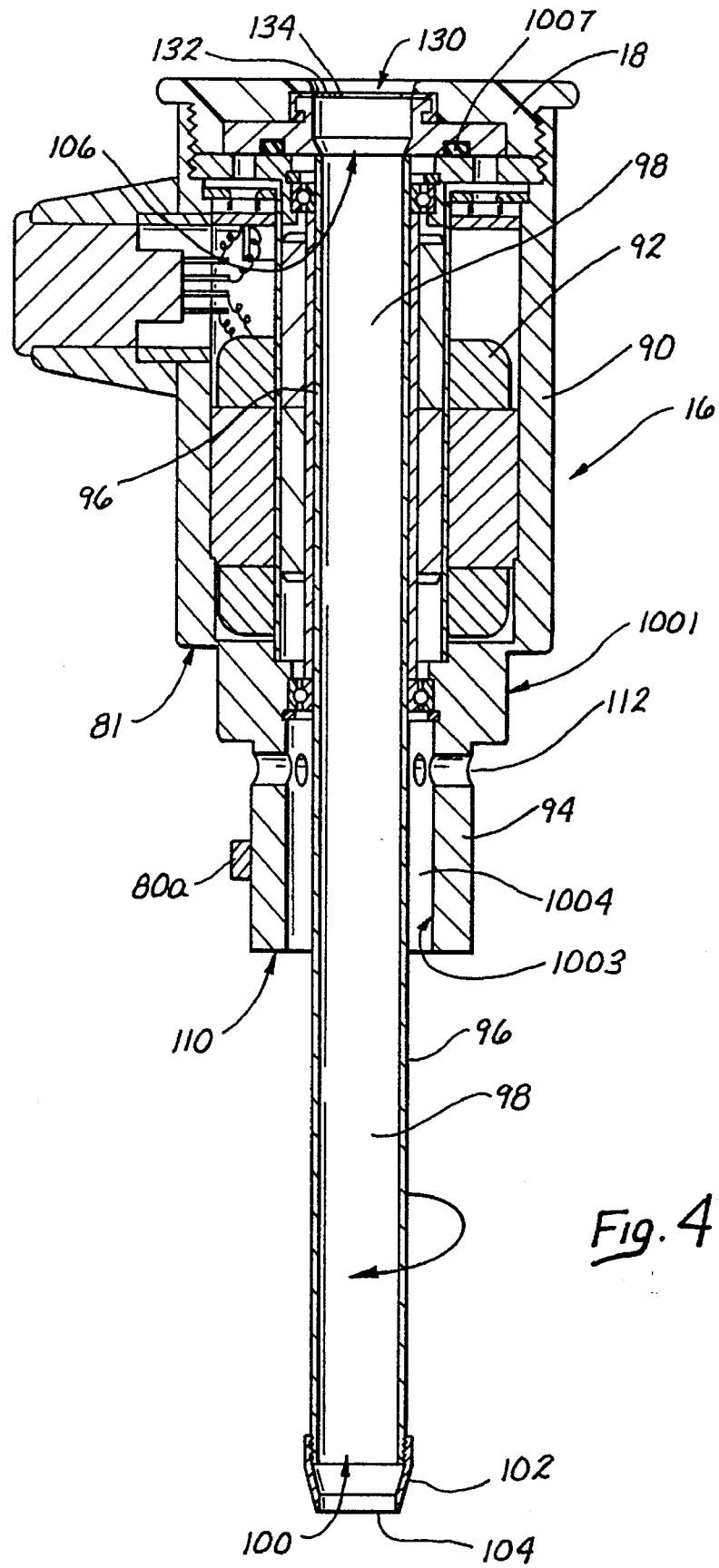
FIG. 4 is a longitudinal sectional view of the hollow-bore morcellator device and pressure-maintaining seal element of the morcellator system shown in FIG. 1.

The preferred pressure-maintaining seal element 18, as shown in FIG. 4, is mounted on top of the hollow-bore morcellator device 16. Such pressure-maintaining seal element 18 comprises a generally round disc formed of plastic or other rigid material, and having a threaded lower portion which threadably engages into the proximal end of motor housing 90, as shown. A proximal central aperture 130 formed in the seal member 18 and a distal aperture 106 formed in the seal member 18 are in alignment with the hollow bore 98 of rotating shaft 96. An O-ring 1007 is provided to form a seal between pressure-maintaining seal element 18 and hollow-bore morcellator device 16 when pressure maintaining seal element 18 is threadably engaged into hollow-bore morcellator device 16. A resilient valving member, such as an elastomeric flap or membrane 132, is positioned transversely within aperture 130. In the preferred embodiment the valving member comprises an elastomeric membrane having a stretchable or expandable round hole 134 formed therein to permit insertion of an elongate tubular suction probe 120 downwardly through the bore 98 of rotating shaft 96. When so inserted, the opening 134 of the membrane 132 will maintain sealing contact about the outer surface of the suction probe 120, thereby preventing loss of suction pressure from suction probe 120, and/or loss of gas pressure from the interior of the pressurized bag 12. The opening 134 formed in the sealing membrane 132 is sufficiently resilient to allow the hereinafter-described suction probe 120 to be moved back and forth within the bore 96 of the rotating shaft 98 while maintaining the desired sealing contact about the suction probe 120. Such back and forth movement of the suction probe 120 enables the probe 120 to contact and repeatedly lift tissue or other matter into contact with the rotating annular cutting tip 102, as described more fully herebelow.

v. Suction Probe/Tissue Containment Chamber Apparatus

Figure 5:
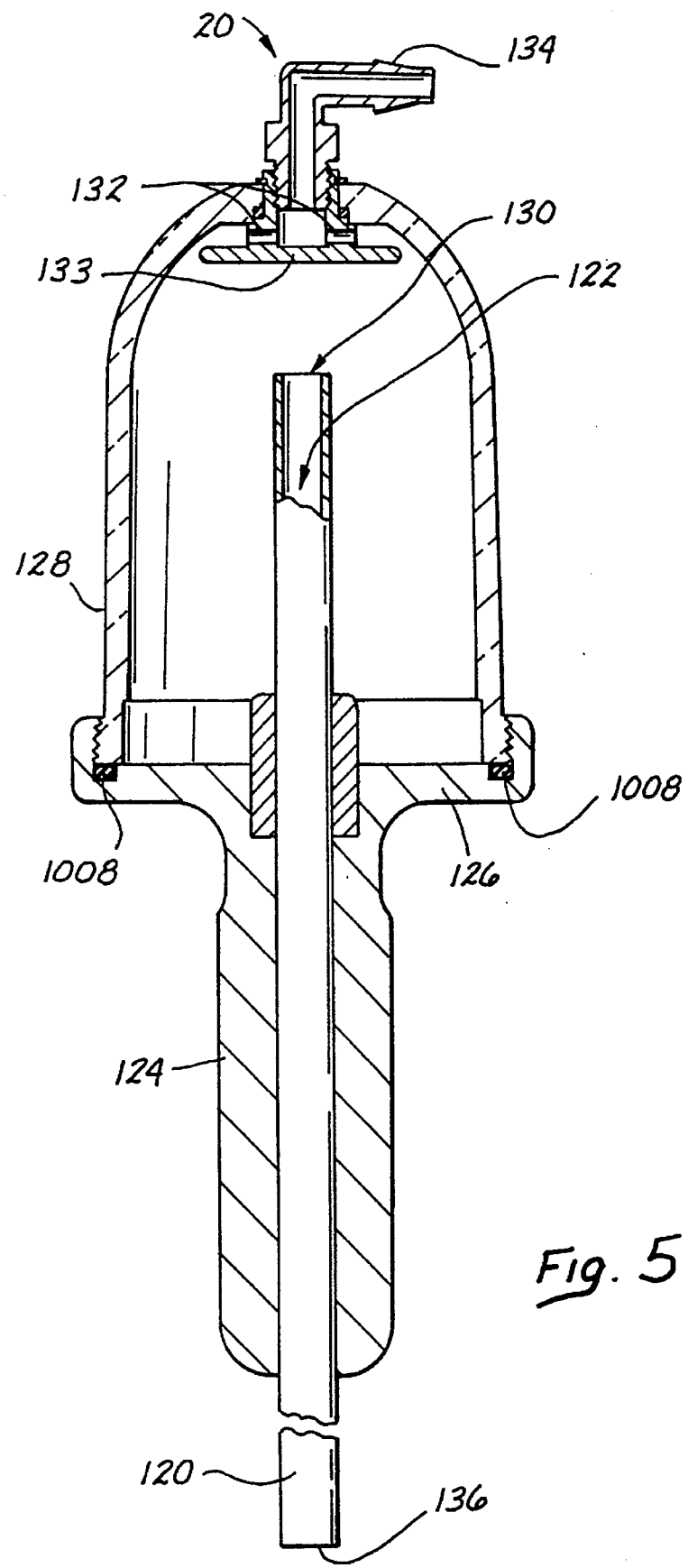
FIG. 5 is a longitudinal sectional view of the suction probe/tissue containment chamber of the morcellator system shown in FIG. 1.

The preferred suction probe/tissue containment chamber apparatus 20 of the present invention is shown in detail in FIG. 5. As shown, the apparatus 20 comprises an elongate tubular suction probe 120 having a hollow suction lumen 122 extending longitudinally therethrough. A rigid plastic handle 124 is formed about a proximal portion of the tubular suction probe 120. A base or flange extends radially about the suction probe 120 and forms the floor 126 of a collection chamber. A clear plastic dome 128 is mountable on the floor 126 of the collection chamber, and in combination therewith forms a matter-receiving vessel or chamber on the proximal end of the suction probe 120. The proximal-most portion of the suction probe 120 stands or protrudes upwardly in the center of the dome 128, such that the proximal opening 130 of the suction probe 120 is located in approximately the upper ⅓ of the dome 128. Thus, the proximal portion of the probe 120 forms a vertical stand pipe within the interior of the collection chamber dome 128 such that plugs of tissue or matter collected in the dome will not prematurely block or interfere with proximal end opening 130 of the lumen 122 of the suction probe 120. Dome 128 is preferably formed of a rigid transparent plastic such as polycarbonate to allow easy visualization of tissue sample collection. Dome 128 threadably engages into handle 124 to allow easy removal of tissue samples. An O-ring 1008 provides a gas-tight seal between dome 128 and handle 124.

A suction tubing connector 134 is mounted on top of dome 128, as shown. A round buffet member or deflector plate 133 is mounted transversely within the interior of the dome 128, immediately beneath the point at which the suction tubing connector 134 enters the interior of the top end of the dome 128. A plurality of suction passageways 132 are formed on the upper side of deflector plate 133 to permit gas to be withdrawn from the interior of the dome 128 into suction tubing connector 134. The deflector plate 133 is configured to substantially prevent tissue or other matter from entering the suction passageways 132 or suction tubing connector 134, thereby preventing inadvertent blockage or clogging of the passageways 132, connector 134 and/or attendant suction apparatus. By such arrangement, suction tubing may be connected to suction tubing connector 134 to apply suction force to the interior of the collection chamber, and through the lumen 122 of the tubular suction probe 120. Morcelled tissue or other matter exiting the proximal end opening 130 of the suction probe 120 may impinge against the underside of deflector plate 133.

The outer diameter of the tubular suction probe 120 is slightly smaller than the inner diameter of the rotating tubular shaft 96 of the hollow-bore morcellator device 16. This allows the tubular suction probe 120 to be inserted downwardly through the opening 134 of pressure-maintaining seal element 18, and freely through the hollow bore 98 of rotating tubular shaft 96. The outer diameter of the tubular suction probe 120 is precisely sized to just slidably pass through the distal opening 104 of cutting ring 102. The suction probe 120 is long enough to pass fully through and out of the distal end of the rotating tubular shaft 96, such that the open distal end 136 of the suction probe 120 may be advanced downwardly beyond the annular cutting tip 102, and into contact with a mass of tissue or other matter T contained in the containment bag 12. The negative pressure being applied to the lumen 122 of the suction probe 120 will cause the distal end 136 of the probe 120 to attach by suction force to a mass of tissue or other matter T. Thereafter, the probe 120 may be retracted in the proximal direction to lift the mass of matter or tissue T into contact with the cutting edge 104 of the rotating annular cutting tip 102. The rotating annular cutting tip 102 will then cut a cylindrical plug or bolus of the matter or tissue T and such cylindrical plug or bolus of tissue will be drawn upwardly, through the lumen 122 of the suction probe 120 and into the tissue containment chamber.

Due to the pliability of the cylindrical plug or bolus of the biological matter or tissue T, even if the diameter of the matter or tissue T exceeds that of the lumen 122 of the suction probe 120, the suction pressure within the lumen 122 is sufficient to facilitate the compression of the matter or tissue T such that the same is drawn upwardly through the lumen 122. Additionally, since the diameter of the annular cutting ring 102, and in particular the cutting edge 104 thereof, does not substantially exceed the inner diameter of the lumen 122, the cylindrical plug or bolus of tissue T is roughly equal in size to the lumen 122 and need not be substantially compressed to be drawn upwardly thereinto by the suction pressure therewithin.

PREFERRED METHOD OF OPERATION AND ASSOCIATED APPARATUS USED THEREFORE

The above-described components of the system 10 are preferably utilized in combination with one another to reduce and remove a mass of tissue or other matter T from an anatomical cavity or space. A presently preferred method for carrying out such procedure is illustrated, in step-wise fashion, in FIGS. 7a–7g.

After the surgeon has excised, resected or disconnected the tissue and/or other matter to be removed, a bag introducer 100 is inserted into the body, through the previously-formed minimal access incision (e.g., less than 3 cm in length). It will be appreciated that a standard laparoscopy trocar or other portal apparatus may have already been inserted into the incision, and the bag introducer 100 may be passed through such trocar or portal, rather than directly through the incision itself.

After the tubular bag introducer 100 has been inserted through the minimal access incision, a grasper 510 or other laparoscopic instrument is introduced via a secondary portal and is utilized to grab tab 1000 and to pull the collapsed containment bag 12 out of the distal end of the introducer 100 and into the anatomical cavity or space. Bag introducer 100 is provided with a seal means 500 to prevent gas leakage around bag inflation tube 34. In a preferred embodiment, seal means 500 is formed of an elastomeric material such as silicone rubber with a slit formed therewithin, allowing inflation tube 34 to pass through and to be slideably moveable while maintaining a gas-tight Seal.

Figure 7A:
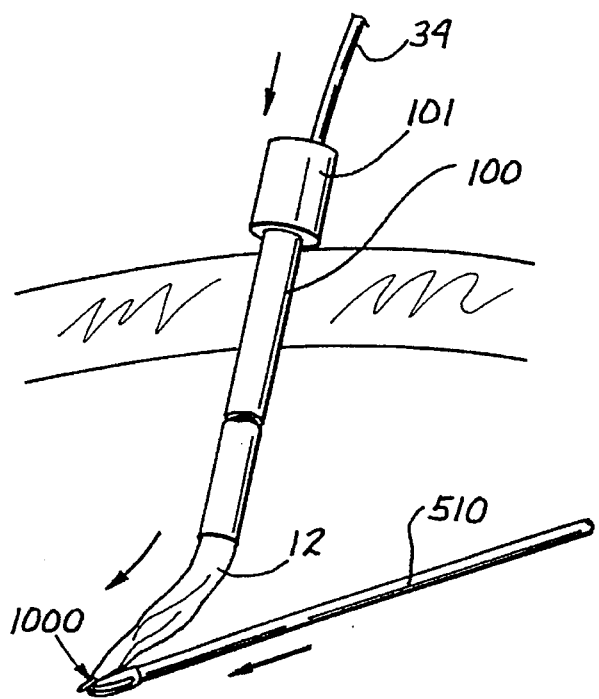
FIG. 7a–7g is a step-wise illustration of a presently preferred method of using the tissue morcellation system of FIG. 1.
Figure 7B:
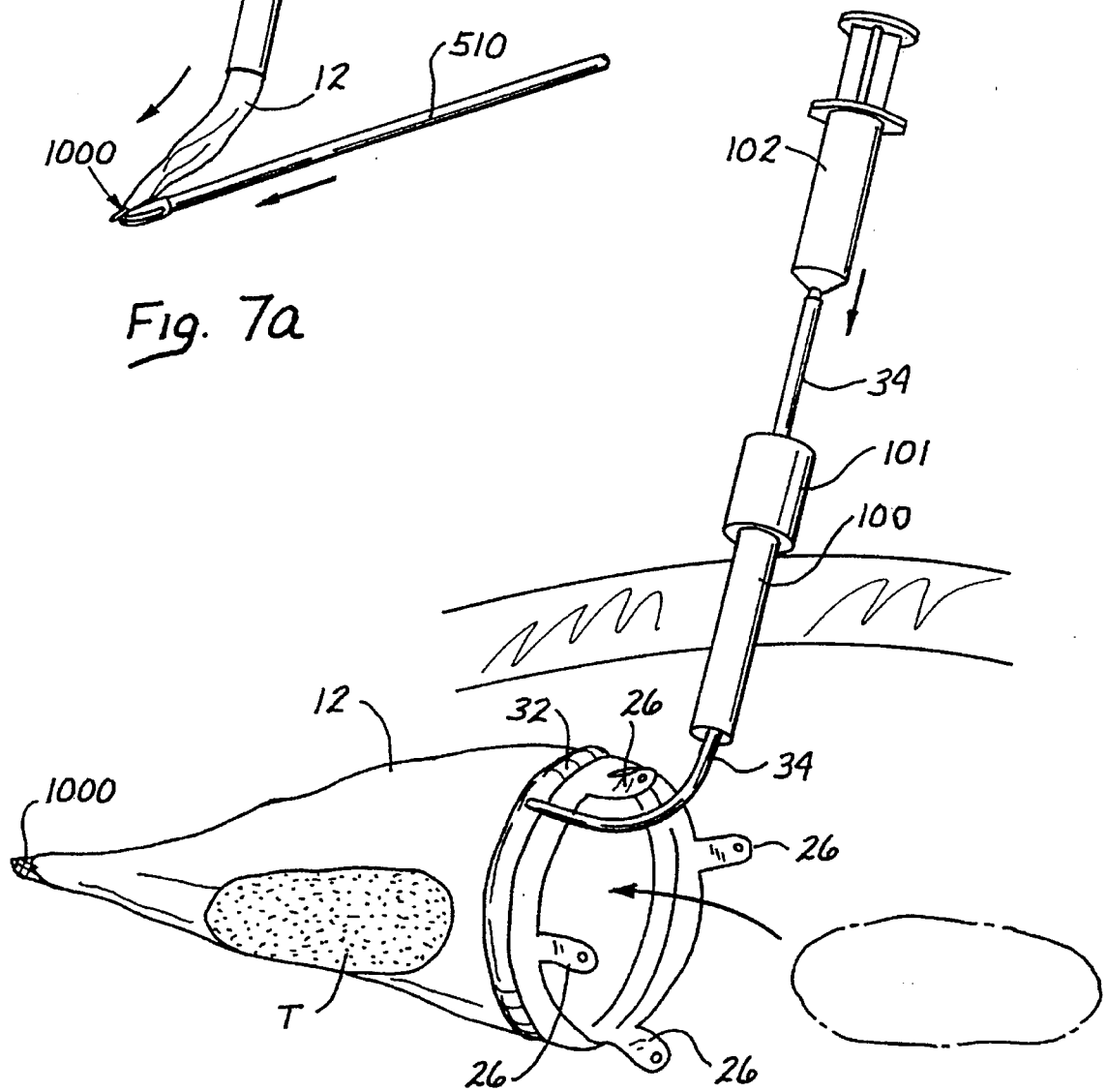

A syringe 102 is connected to the bag inflation tube 34 to facilitate inflation of the air bladder 32 formed about the mouth 24 of the bag 12. Such inflation of the air bladder 32 will cause the mouth 24 of the bag 12 to open. (FIG. 7b)

After the mouth 24 of the bag 12 has been opened, the bolus of tissue or other matter T to be removed is passed into the interior of the bag 12. Thereafter, the syringe 102 is utilized to withdraw the inflation fluid from the air bladder 32, thereby emptying the air bladder 32 and allowing the mouth of the bag 12 to collapse.

Figure 7C:
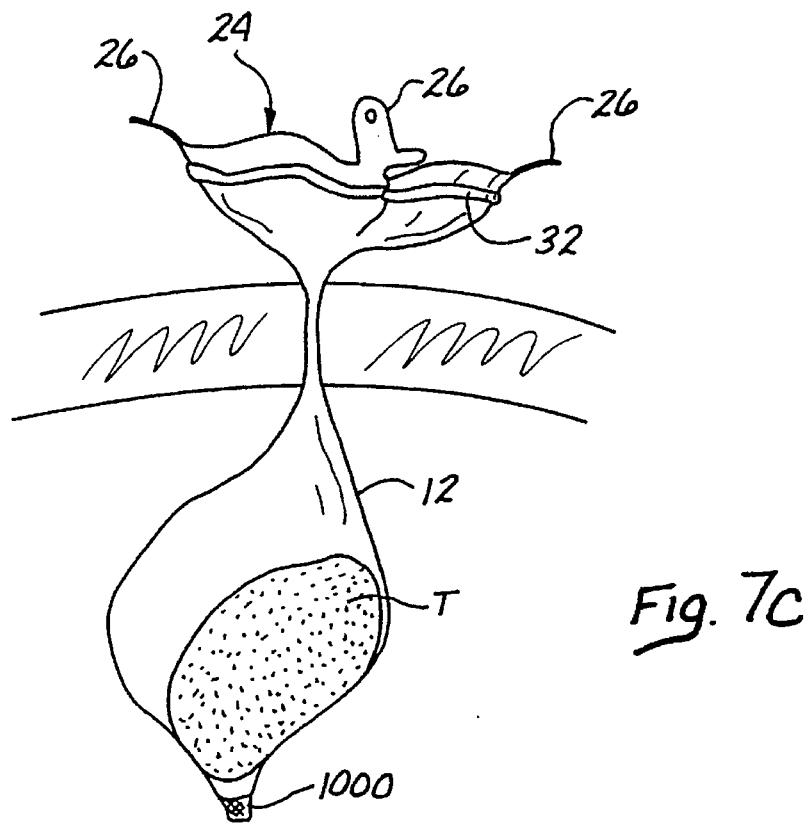

Thereafter, the introducer 100 may be extracted and removed, and the collapsed mouth of the bag 12 is withdrawn and exteriorized through the minimal access incision. The body of the bag 12 containing the mass of tissue or other matter T remains within the body. (FIG. 7c)

Figure 7D:
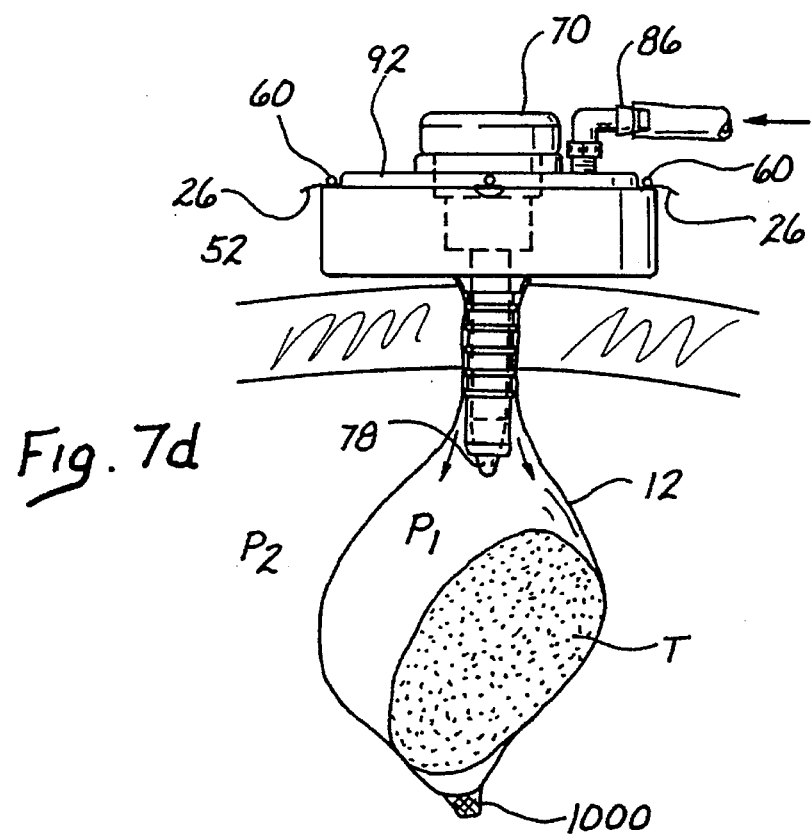

Thereafter, the outer ring 52 of the portal apparatus 14 is inserted about the mouth of the bag 12. The tongues or attachment projections 26 of the bag are grasped and the apertures 28 formed therein are passed over the attachment lugs 60 formed on the upper surface of the outer ring 52. This serves to hold the mouth of the bag in an open configuration in the central bore 54 of the outer ring 52. The obturator 70 is inserted into the inner ring member 42 of the portal apparatus 14 and the combined obturator 70/inner ring member 42 are inserted downwardly into the open mouth of the bag 12 within the central bore 54 of the outer ring 52. When so inserted, O-ring 56 will compress the adjacent material of the bag 12 against the inner surface of the surrounding outer ring 52, thereby forming a substantially gas tight seal between the inner surface of the bag 12 and the outer surface of the inner ring member 42. (FIG. 7d)

Figure 7E:
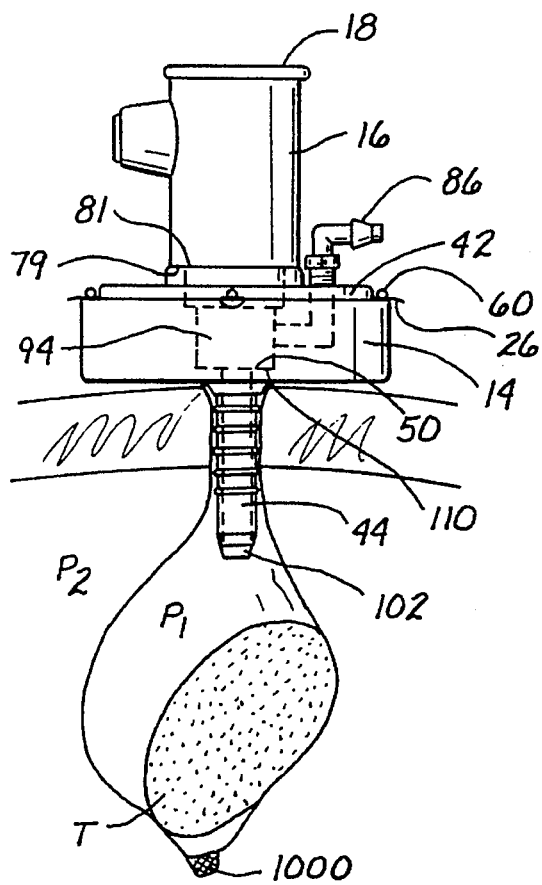

The morcellator device 16 is prepared for use by attachment of the pressure maintaining seal element 18 to the top or proximal end thereof, and connecting the annular cutting ring 102 to the bottom or distal end thereof. Thereafter, when it is desired to reduce and remove the mass of matter or tissue T, the disk-shaped upper plug portion 72 of the obturator 70 is grasped and turned to disengage the lugs 80 of the obturator 70 from the serpentine engagement keyways 64. The entire obturator 70 is then removed from the portal apparatus 14. The morcellator device 16 is then inserted downwardly through the inner ring member 42 of the portal apparatus 40 such that the engagement lugs 80a of the morcellator device 16 pass into the serpentine engagement keyways 64 of the portal apparatus 14. The morcellator device 16 is then turned to fully engage the engagement lugs 80a into the basil portions of the serpentine keyway 64, thereby firmly holding the morcellator device 16 within the surrounding portal apparatus 14. When so positioned, the lower surface 110 of the lower housing portion 94 of the morcellator device 16 will rest on the abutment shoulder 50 of the inner ring member 42 of the portal apparatus 14, lower surface 81 will rest on the upper rim 79 of the inner ring member 42 of portal apparatus 14, and the hollow rotating shaft 96 of the morcellator device 16 will extend downwardly through the lower tubular projection 44 of the portal apparatus 14, such that the annular cutting ring 102 of the morcellator device 16 protrudes beyond the distal end of the lower tubular projection 44 of the portal apparatus 14. (FIG. 7e)

The positive pressure gas being infused through tubing connector 86 and gas inlet passageway 84 will pass through the luminal space 48 which remains between the outer surface of the rotating hollow shaft 96 and the surrounding inner luminal surface of the tubular projection 44 of the portal apparatus 14 and out through holes 1005 formed in tubular projection 44. In this manner, the desired pressure $P_1$ is maintained within the interior of the bag 12, relative to the surrounding pressure $P_2$ within the body cavity or space.

When it is desired to begin morcellation and removal of the tissue or other matter T, the distal end 136 of the suction probe 120 of suction probe/tissue containment apparatus 20 is inserted downwardly through the aperture 134 of the pressure maintaining valving member 18 and through the hollow central bore 98 of the morcellator device 16. The valving member 132 of the sealing member 18 forms a substantially gas tight seal about the outer surface of the suction probe 120, while allowing the suction probe 120 to remain slideably movable up and down within the bore 98 of the morcellator device 16. The motor 92 of the morcellator device 16 is energized, causing the hollow shaft 96 and annular cutting ring 102 to rotate at a preferred rotational speed of 2,000–6,000 rpm. The suction probe 120 is initially inserted downwardly to a point where the distal end 136 of the probe 120 compresses against and draws suction upon the mass of tissue or other matter T within the containment bag 12. (FIG. 7 F)

Figure 7G:
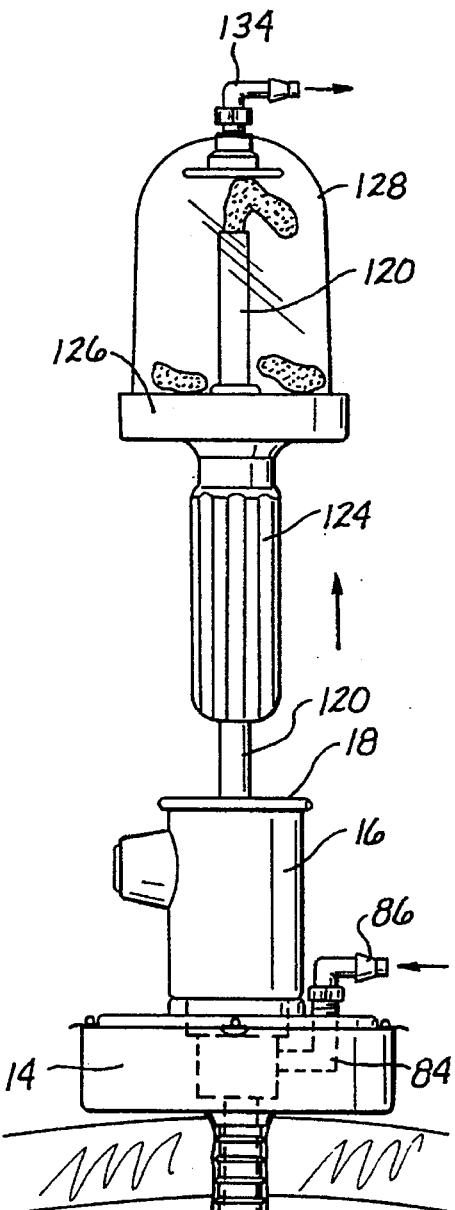
Figure 7F:
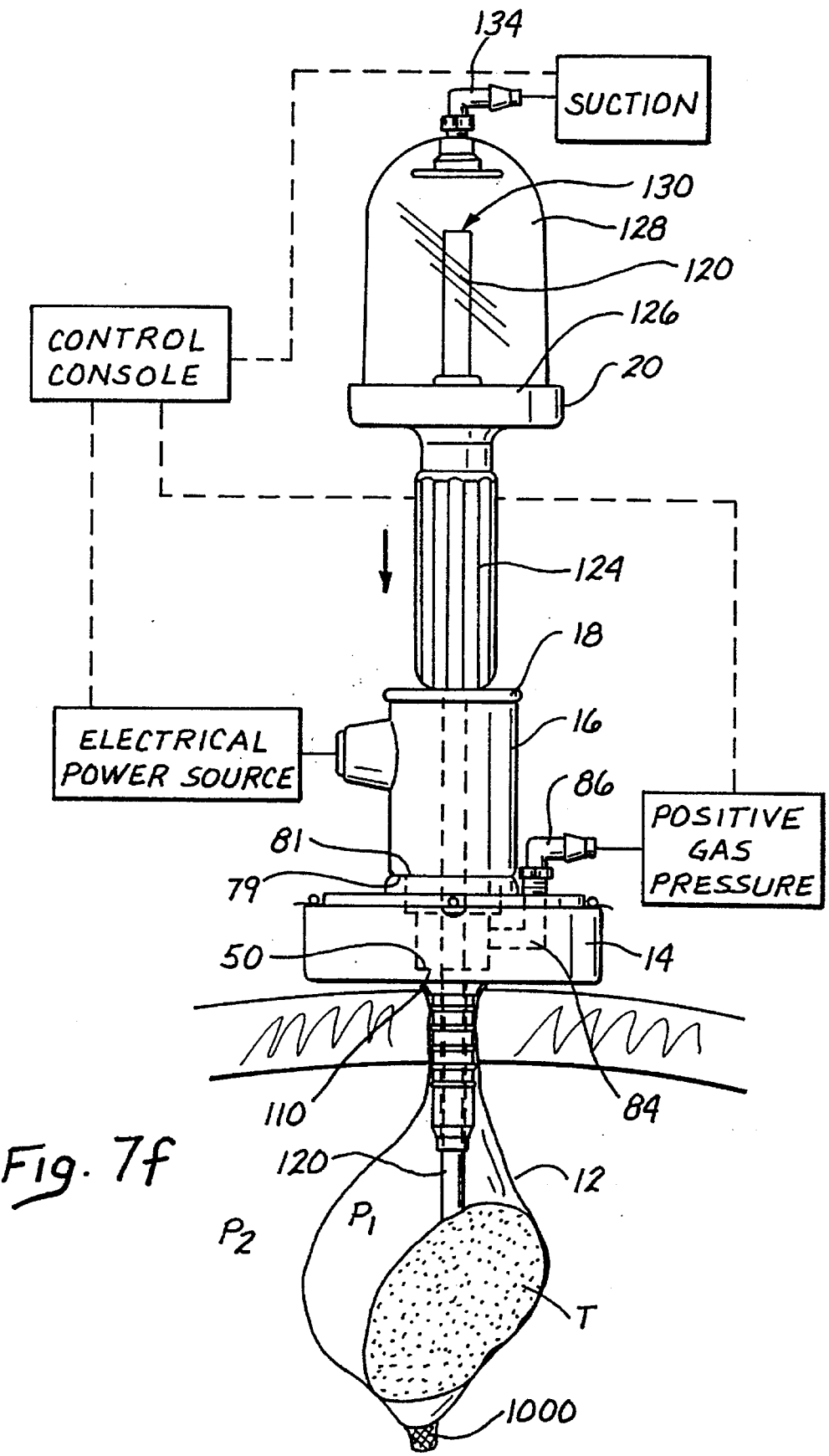

The probe 120 is then pulled upwardly, thereby lifting the massive tissue or other matter T into contact with the rotating annular cutting ring 102 of the morcellator device 16. The cutting ring 102 cuts a generally cylindrical plug or mass from the tissue or other matter T, and the separated plug or mass is drawn by suction pressure upwardly through the inner bore 122 of the suction probe 120 and into the interior of the collection chamber. Such up and down movement of the suction probe 120 is carried out repeatedly until the entire mass of tissue or other matter T has been cut into plugs or boluses of tissue which have been drawn upwardly through the bore 122 of the suction probe 120 and collect within the collection chamber. (FIG. 7g)

Thus, by the above-described method, the morcellator system 10 of the present invention is used to remove the entire mass of tissue or other matter T from the space or body cavity, without requiring enlargement of the minimal access incision, and without dissemination or leakage of fragments or pieces of tissue or other matter T into the body.

It will be appreciated that the invention has been described herein with reference to specific preferred embodiments of the invention. It will be appreciated that the invention may take physical form or, be utilized in, various other embodiments which differ from those described herein. Accordingly, it is intended that all embodiments within the intended spirit and scope of the invention be included within the following claims.

What is claimed is:

1. A tissue morcellation system comprising:

a portal apparatus having an opening extending therethrough, said portal apparatus being insertable through an incision formed in a mammalian body such that the opening of the portal apparatus provides a passageway into the mammalian body;

a morcellator device insertable through the opening of said portal apparatus, said morcellator device comprising;
   i) a drive motor;
   ii) a shaft extending downwardly from said drive motor and being rotatable thereby, said shaft having a distal end;
   iii) a cutting element positioned on the distal end of said shaft; and
   iv) a hollow passageway which extends longitudinally through said drive motor, through said shaft, and through said cutting element; and an elongate, non-rotatable suction probe having a proximal end, a distal end, a suction lumen extending longitudinally therethrough and an outer surface, said suction probe being operatively coupled to a vacuum source for selectively creating suction pressure within the suction lumen, and insertable through the hollow passageway and moveable back and forth within said passageway such that the distal end of the probe will engage, by suction pressure, a mass of matter located within said mammalian body and will lift said mass of matter into contact with the cutting element of said morcellator device such that a portion of said mass of matter may be severed by said cutting element and drawn out of the body through the lumen of said suction probe.

2. The system of claim 1 further comprising:

a containment sac for containing said mass of matter within the body, said containment sac having a mouth through which the shaft of the morcellator device, and the suction probe, may be inserted.

3. The system of claim 2 wherein said containment sac mouth is deployable in relation to the opening of said portal apparatus such that, when the morcellator device is inserted into the opening of said portal apparatus, the shaft of the morcellator device will extend into said containment sac.

4. The system of claim 2 further comprising:

a gas inlet passageway formed in said portal apparatus to permit positive pressure gas to be infused into said containment sac.

5. The system of claim 2 wherein said portal apparatus comprises:

an outer ring member;

an inner ring member positionable within said outer ring member, said inner ring member having said opening extending downwardly therethrough, said inner ring member having an outer surface which is configured to nest within said outer ring member, in abutting contact with said outer ring member.

6. The system of claim 5 wherein the mouth of said containment sac is extractable from said mammalian body through said incision and initially deployable within said outer ring member such that, when said inner ring member is nested within said outer ring member, the containment sac will be compressively held between said inner ring member and said outer ring member, such that the central opening in said inner ring member provides a passageway which leads into the containment sac.

7. The system of claim 2 wherein said containment sac further comprises:

a plurality of first connectors formed about the mouth of said containment sac;

and wherein said portal apparatus further comprises:

a plurality of second connectors formed on said portal apparatus, said second connectors on said portal apparatus being connectable to said first connectors on said containment sac to hold said containment sac in a substantially fixed position relative to said portal apparatus.

8. The system of claim 2 further comprising means for infusing fluid into said containment sac to maintain sufficient pressure within the sac to prevent the said sac from collapsing.

9. The system of claim 8 wherein:

said portal apparatus is constructed to engage and hold the mouth of said tissue containment sac such that, when said morcellator device is inserted through said opening of said portal apparatus, the morcellator device will extend into said containment sac; and said means for controlling the pressure within said containment sac comprises a gas infusion pathway formed in said portal apparatus for infusing gas into said containment sac.

10. The system of claim 9 wherein said morcellator device, said portal apparatus and said containment sac are configured such that, when said morcellator device is inserted into the opening of said portal apparatus, a seal is formed between said morcellator device and said portal apparatus to prevent leakage therebetween of gas from the interior of said containment sac.

11. The system of claim 8 further comprising:

means for coordinating the mass flow of gas infused into the containment sac with the mass flow of gas withdrawn through said suction probe to maintain at least a minimum pressure within said containment sac.

12. The system of claim 8 further comprising:

means for coordinating the mass flow of gas infused into said containment sac with the volume of gas removed from containment sac through said suction probe, to thereby maintain at least a predetermined minimum pressure within said containment sac to prevent collapse thereof.

13. The system of claim 12 wherein said means for coordinating comprises:

means for infusing a pressure-regulated mass flow of make-up gas into said containment sac, said mass flow of make-up gas being adequate to maintain said sufficient pressure within said sac to prevent said sac from collapsing when gas is removed from said sac through said suction probe.

14. The system of claim 1 wherein said suction probe further comprises:

a containment vessel positioned on the proximal end of said suction probe to receive and contain matter which has been separated from said mass of matter by said cutting element, and which has subsequently been aspirated through said suction probe.

15. The system of claim 14 wherein a proximal portion of the suction probe extends into said containment vessel.

16. The system of claim 15 wherein said containment vessel is vertically disposed during use and defines upper, middle, and lower interior regions, and wherein said proximal portion of said suction probe extends into the upper interior region of said containment vessel.

17. The system of claim 1 wherein said portal apparatus comprises:

a rigid body having the opening extending downwardly therethrough, said rigid body incorporating a lower portion which is sized and configured to pass through an incision of approximately 1 cm in length.

18. The system of claim 17 wherein:

the opening of said portal apparatus is analogous in size and configuration to portions of said morcellator device, such that said morcellator device may be nested within the central opening of said portal apparatus.

19. The system of claim 1 wherein said portal apparatus further comprises:

an obturator member insertable into the opening of said portal apparatus to close off said opening of said portal apparatus.

20. The system of claim 19 wherein said portal apparatus further comprises:

means for engaging and holding said obturator member within said portal apparatus.

21. The system of claim 20 wherein said means for engaging and holding said obturator comprises:

at least one lug formed on said obturator member; and at least one receiving groove formed in said portal apparatus to receive and frictionally hold said lug of said obturator member.

22. The system of claim 20 wherein said morcellator device is sized and configured to nest within and be supported by the opening of said portal apparatus.

23. The system of claim 22 wherein said morcellator device further comprises:

means for engaging and holding said morcellator device within said portal apparatus.

24. The system of claim 23 wherein said means for engaging and holding said morcellator device comprises:

at least one lug formed on said morcellator device; and at least one receiving groove formed in said portal apparatus to receive and frictionally hold said lug of said morcellator device.

25. The system of claim 1 wherein the cutting element of said morcellator device comprises an annular cutting ring positioned on the distal end of said shaft.

26. The system of claim 13 wherein said annular cutting ring is removable from said shaft.

27. The system of claim 13 wherein said annular cutting ring has an annular cutting edge formed on the distal end thereof, such that when a mass of matter having a diameter larger than that of said cutting ring is lifted into contact with said cutting ring, the distal cutting edge of said cutting ring will sever a generally cylindrical portion of said mass.

28. The system of claim 1 further comprising:

a seal element associated with the hollow passageway of said morcellator device to prevent backflow of gas through said passageway.

29. The system of claim 27 wherein said seal element comprises a sealing member positionable on top of said drive motor, said sealing member having an opening formed therein in alignment with said hollow passageway of said morcellator device, and an elastomeric seal disposed transversely within said passageway said elastomeric seal having an opening formed therein such that:

i) when said suction probe is not inserted into said hollow passageway, said opening will be no larger in cross sectional area than said suction probe, thereby limiting the mass flow of gas which may escape through said hollow passageway, and ii) when said suction probe is inserted through said hollow passageway, said opening will seal about said suction probe to form a substantially gas tight seal around said suction probe, while allowing said suction probe to be moved back and forth within said hollow passageway.

30. A morcellator device for morcelling matter within a mammalian body, said device comprising:

a drive motor;

a shaft extending downwardly from said drive motor, said shaft having a distal end;

a cutting element positioned on the distal end of said shaft;

a hollow passageway which extends longitudinally through said drive motor, through said shaft, and through said cutting element; and an elongate suction probe having a proximal end, a distal end, a suction lumen extending longitudinally therethrough and an outer surface, said suction probe being operatively coupled to a vacuum source for selectively creating suction pressure within the suction lumen;

said drive motor being operative to rotatably drive said shaft and said cutting element such that, while said shaft and said cutting element are rotating, said suction probe may be passed through said hollow passageway and moved back and forth therewithin beyond said cutting element such that the distal end of said suction probe may engage, by suction pressure, a mass of matter located beyond said cutting element, and subsequently move said mass of matter into contact with said cutting element so as to effect morcellation of said mass of matter by said cutting element in a manner wherein a portion of said mass of matter is severed by said cutting element and drawn through the suction lumen of said suction probe.

31. The morcellator device of claim 30 further comprising:

a containment chamber connected to the proximal end of said suction probe for receiving and collecting portions of said mass of matter which have been drawn through the suction lumen of said suction probe.

32. A method for morcelling and removing a mass of matter located within a mammalian body, said method comprising:

a) forming an incision of less than 3 cm in said mammalian body;

b) inserting, through said incision, a morcellator device comprising:

a drive motor;

a shaft extending downwardly from said drive motor, said shaft having a distal end;

a cutting element positioned on the distal end of said shaft; and a hollow passageway which extends longitudinally through said drive motor, through said shaft, and through said cutting element;

said drive motor being operative to rotatably drive said shaft and said cutting element such that, while said shaft and said cutting element are rotating, a separate suction probe operatively coupled to a vacuum source for selectively creating suction pressure therewithin may be passed through said hollow passageway and beyond said cutting element to engage, by suction pressure, a mass of matter located beyond said cutting element, and to subsequently move said mass of matter into contact with said cutting element so as to effect morcellation of said mass of matter by said cutting element;

c) energizing the drive motor of said morcellator device to cause said shaft and said cutting element to rotate;

d) advancing the suction probe through the hollow passageway of said morcellator device until said suction probe engages, by suction pressure, the mass of matter located within said mammalian body;

e) retracting said suction probe to lift said mass of matter into contact with the rotating cutting element of said morcellator device such that a portion of said mass of matter will be severed by said cutting element and drawn, out of the mammalian body, through said suction probe.

33. The method of claim 32 wherein said method further comprises:

f) repeating steps d and e until the entire mass of matter has been removed from said mammalian body.

34. The method of claim 32 further comprising:

g) providing a collection chamber connected to said suction probe such that the portions of the mass of matter drawn through the suction probe will be received and collected within said collection chamber.

35. The method of claim 32 further comprising:

initially inserting a tissue containment sac having an opening formed therein, through said incision and into said mammalian body;

placing said mass of tissue within said containment sac;

drawing the opening of said containment sac out of said incision while allowing the remainder of said containment sac, with said mass of matter contained therein, to remain within said body, and, wherein;

the insertion of the morcellator device in step b), is accomplished by inserting said morcellator device into said containment sac.

36. The method of claim 35 further comprising:

infusing positive pressure gas into said containment sac to maintain a pressure within said containment sac which is greater than the surrounding pressure within said mammalian body, to thereby prevent said containment sac from collapsing.

\* \* \* \* \*